United States Patent [19]

Shikhman et al.

[11] Patent Number: 5,423,796
[45] Date of Patent: Jun. 13, 1995

[54] TROCAR WITH ELECTRICAL TISSUE PENETRATION INDICATOR

[75] Inventors: Oleg Shikhman, Bridgeport, Conn.; Sidney D. Autry, Bellingham, Wash.

[73] Assignee: United States Surgical Corporation, Norwalk, Conn.

[21] Appl. No.: 135,601

[22] Filed: Oct. 8, 1993

[51] Int. Cl.⁶ .............................. A61M 5/178
[52] U.S. Cl. ...................... 606/1; 606/167; 606/185; 604/164
[58] Field of Search ......... 606/167, 184, 185, 32, 606/37, 39, 45, 48, 28, 29; 604/164

[56] References Cited

U.S. PATENT DOCUMENTS

| | | | |
|---|---|---|---|
| 3,595,239 | 7/1971 | Petersen | 606/45 |
| 4,269,192 | 5/1981 | Matsuo . | |
| 4,299,230 | 11/1981 | Kubota . | |
| 4,356,826 | 11/1982 | Kubota . | |
| 4,535,773 | 8/1985 | Yoon . | |
| 4,582,061 | 4/1986 | Fry . | |
| 5,066,288 | 11/1991 | Deniega et al. . | |
| 5,083,573 | 1/1992 | Arms . | |
| 5,209,721 | 5/1993 | Wilk . | |
| 5,215,526 | 6/1993 | Deniega et al. | 604/164 |
| 5,217,441 | 6/1993 | Shichman . | |
| 5,221,281 | 6/1993 | Klicek | 606/45 |
| 5,224,952 | 7/1993 | Deniega et al. | 604/164 X |
| 5,263,937 | 11/1993 | Shipp | 604/164 |
| 5,271,380 | 12/1993 | Riek et al. . | |

FOREIGN PATENT DOCUMENTS

| | | |
|---|---|---|
| 836392 | 8/1951 | Germany . |
| 1616107 | 4/1971 | Germany . |
| 537677 | 1/1977 | U.S.S.R. . |
| WO14514 | 9/1992 | WIPO ................ 606/45 |

*Primary Examiner*—Peter A. Aschenbrenner

[57] ABSTRACT

The present invention relates to a trocar adapted to provide a surgeon with an indication when the trocar has penetrated body tissue. The trocar includes an obturator assembly and a cannula assembly. The obturator assembly has an obturator housing and an obturator shaft. The shaft has a proximal end portion connected to the housing and a distal end portion adapted to conduct electricity and penetrate body tissue. An electric connection assembly is associated within the obturator housing and provides a conductive path between the conductive portion of the obturator shaft and an outer surface portion of the obturator housing. The connection assembly is also adapted to receive an external electrical connector.

4 Claims, 12 Drawing Sheets

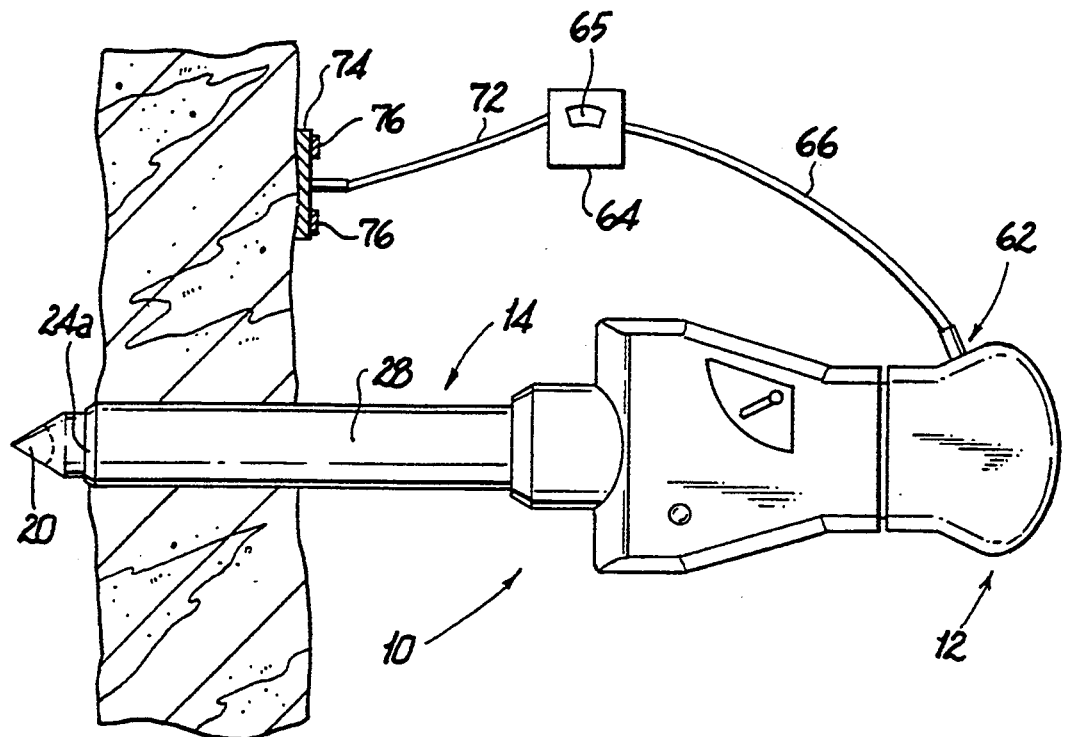
FIG. 12
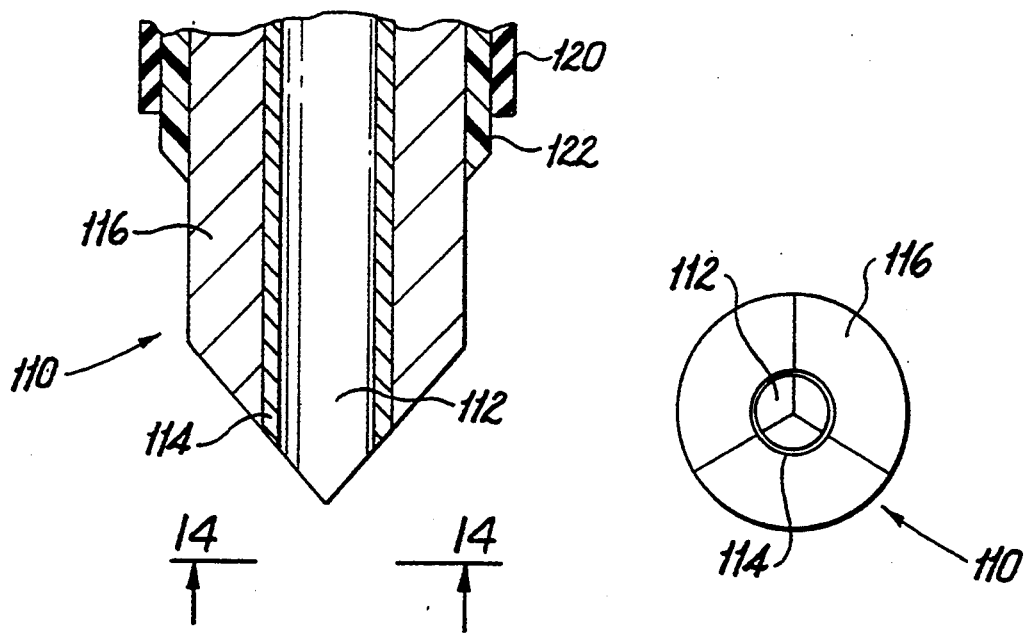
FIG. 13
FIG. 14

TROCAR WITH ELECTRICAL TISSUE PENETRATION INDICATOR

BACKGROUND OF THE INVENTION

1. Field of the Invention

The present invention relates to an apparatus for penetrating body tissue. More particularly, the present invention relates to a trocar assembly having an electrical tissue penetration indicator.

2. Description of the Related Art

Endoscopic surgical procedures, that is, surgical procedures performed through tubular sleeves or cannulas, have been utilized for many years. Initially, endoscopic surgical procedures were primarily diagnostic in nature. More recently as endoscopic technology has advanced, surgeons are performing increasingly complex and innovative endoscopic surgical procedures. In endoscopic procedures, surgery is performed in any hollow viscus of the body through a small incision or through narrow endoscopic tubes either (or cannulas) inserted through small entrance wounds in the skin. In laparoscopic procedures surgery is performed in the interior of the abdomen.

Laparoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated. Moreover, laparoscopic and endoscopic procedures often require the surgeon to act on organs, tissues and vessels far removed from the incision, thereby requiring that any instruments to be used in such procedures be both long and narrow.

Typically, after the surgical region is insufflated, trocars are used to puncture the body cavity and provide the above noted cannula used during endoscopic procedures. Generally, trocars used during such procedures include a styler having a sharp tip for penetrating the body cavity positioned coaxially within protective tubes to protect a patient or surgeon from inadvertent contact with the tip. An example of a known trocar is described in commonly assigned, U.S. Pat. No. 4,601,710 to Moll. Most currently used trocars rely on protective tubes to prevent inadvertent contact with the tip, which utilize intricate mechanical designs to achieve the desired protective feature.

Another type of trocar used for penetrating body tissue is described in European Patent Application No. 0 484 725. That trocar has a hollow shaft and a tip at a distal end portion of the hollow shaft formed as a window made from a suitable transparent material, such as glass quartz or glass plexiglass. An optic guide and a fiber optic lighting unit are fed to the tip through the hollow shaft. Typically, the optic includes fiber optic light guides which are fed through the hollow shaft to the tip. The optic ends at an axial distance behind the vertex point of the tip so that the optic illuminates the entire lateral surface of the conical window for observation purposes. In this configuration, the operator has an interior view of the structures that will be penetrated when inserting the instrument. Thus, the operator can, for example, detect blood vessels before they are encountered by the tip of the instrument and avoid them. More particularly, the operator can observe the distal end of the tip when penetrating the peritoneum and after complete penetration so that the subjacent vessels and structures of the peritoneum are avoided.

The present invention provides a new and different apparatus and method for detecting penetration of the peritoneum or other body portions with a trocar assembly.

SUMMARY OF THE INVENTION

A trocar is provided to facilitate insertion of surgical instruments into body Cavities. The trocar includes an obturator housing and an obturator. The obturator includes an obturator shaft extending from the housing and an obturator tip secured to a distal end of the obturator shaft. The obturator tip is fabricated from an electrically conductive material. The trocar also includes a cannula housing having a longitudinal bore extending therethrough for coaxially receiving at least a portion of the obturator. A cannula sleeve defining a longitudinal bore is operatively associated with the bore in the cannula housing and extends outwardly from the housing. Electric connection means is provided and is operatively associated with the obturator housing. The electric connection means provides a conductive path between the conductive distal end portion of the obturator and a circuit energizing source. The trocar also includes means for interrupting the conductive path between the distal end portion of the obturator and the electric connection means upon penetration of the body tissue.

In an alternative embodiment, the trocar includes an obturator housing and an obturator shaft fabricated from an electrically conductive material and having a proximal end portion secured to the obturator housing and a distal end portion adapted to penetrate body tissue. An obturator sleeve fabricated from an electrically insulating material is concentrically positioned about the obturator shaft to limit the exposure of portions of the conductive obturator shaft. A cannula assembly is also provided, which may remain in the body cavity to allow insertion of endoscopic instruments while maintaining a gas tight seal when the trocar assembly is inserted into the body tissue. The cannula assembly includes a cannula housing and a hollow cannula sleeve secured to the cannula housing and extending outwardly therefrom. The cannula housing has an opening therethrough aligned with the opening of the cannula sleeve which is adapted to receive the obturator shaft and the obturator sleeve. A valve system is positioned within the cannula housing to maintain the above noted gas tight seal.

The present invention also includes a method for penetrating body tissue. The method includes a step of providing a trocar for penetrating body tissue. Preferably, the trocar includes an insulating cannula assembly and an obturator assembly having an electrically conductive path between a proximal end portion and a distal end portion. The distal end portion of the obturator assembly is, preferably, configured to penetrate body tissue.

The method also includes the steps of providing indicating means between the conductive path and the body tissue, applying a current to the conductive path so that the current passes through the conductive path and the body tissue when the distal end portion of the obturator assembly contacts the body tissue (i.e., the circuit is completed). Once the circuit is completed, the indicating means activates so the surgeon can monitor the indicating means to determine subsequent penetration. Pressure is then applied to the proximal end of the obturator assembly so that the distal end portion of the obturator assembly penetrates the body tissue and the indicating means deactivates upon penetration.

BRIEF DESCRIPTION OF THE DRAWINGS

The preferred embodiments of the invention are described hereinbelow with reference to the drawings wherein:

FIG. 12 is a top plan view similar to FIG. 11, illustrating sufficient penetration of the conductive portion of the obturator shaft and the insulating obturator sleeve to break the circuit between the body tissue and the trocar assembly, which is measured by the instrument.

FIG. 13 is a partial cross-section of the distal end of another embodiment of the present invention;

FIG. 14 is a view 14—14 of a portion of FIG. 13;

DETAILED DESCRIPTION OF THE PREFERRED EMBODIMENTS

The apparatus of the present invention is provided to penetrate body tissue, e.g., the abdominal wall, and to provide an indication to the physician that the body tissue has been penetrated. In the preferred embodiment, the apparatus is a trocar assembly 10 having an obturator assembly 12 and a cannula assembly 14.

Figure 1:
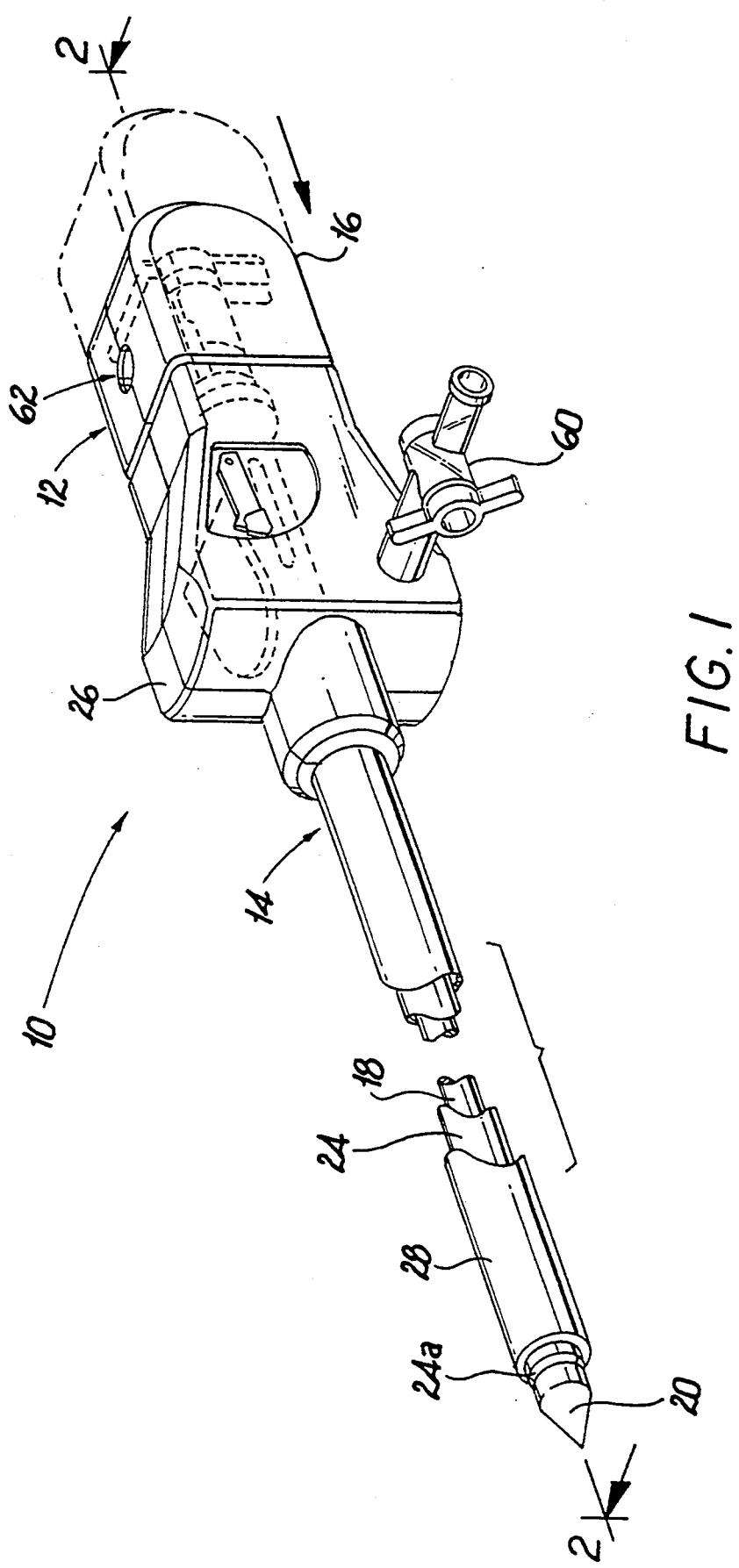
FIG. 1 is a perspective view of an exemplary trocar assembly configured in accordance with the present invention and illustrating a cannula housing having a cannula sleeve extending therefrom which is interfitted with an obturator housing having a conductive obturator shaft and obturator tip within an insulating obturator sleeve.
Figure 2:
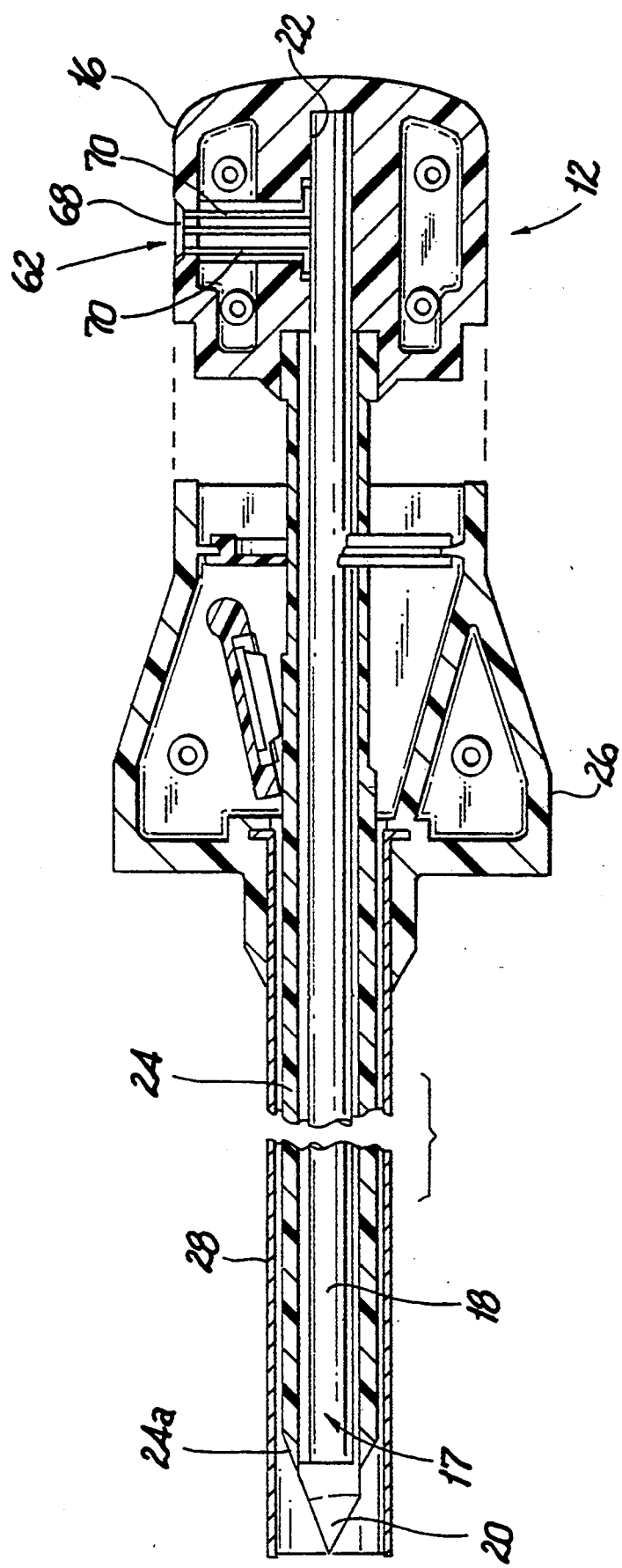
FIG. 2 is a top view in partial cross-section of the trocar assembly of FIG. 1 taken along line 2—2 and illustrating the electrical connection between a connector port and the obturator shaft.

Referring to FIGS. 1 and 2, obturator assembly 12 includes obturator housing 16, obturator 17 which has an obturator shaft 18 and obturator tip 20. The proximal end of obturator shaft 18 is secured within aperture 22 of obturator housing 16 so that the obturator shaft extends outwardly from the obturator housing and obturator tip 20 is secured to the distal end of shaft 18, as shown in FIG. 2. Preferably, obturator sleeve 24 is concentrically positioned about obturator shaft 18 and is secured to the distal end of obturator housing 16, as shown. In this configuration, obturator shaft 18 and obturator tip 20 are fabricated from an electrically conductive material, such as stainless steel, to provide a conductive path between obturator housing 16 and the pointed portion of obturator tip 20. Obturator sleeve 24, on the other hand, is fabricated from an insulating material, such as polytetrafluoroethylene (PTFE), otherwise known as TEFLON which is manufactured by DuPont, to limit exposure of the conductive path and to act as a circuit breaker when the obturator tip penetrates the body tissue.

Cannula assembly 14 includes cannula housing 26 and cannula sleeve 28 secured to the cannula housing and extending outwardly therefrom. Cannula housing 26 is configured and dimensioned to interfit with obturator housing 16, as shown in FIG. 1, so that obturator shaft 18 slides within cannula sleeve 28 when the two assemblies are interfitted.

Figure 3:
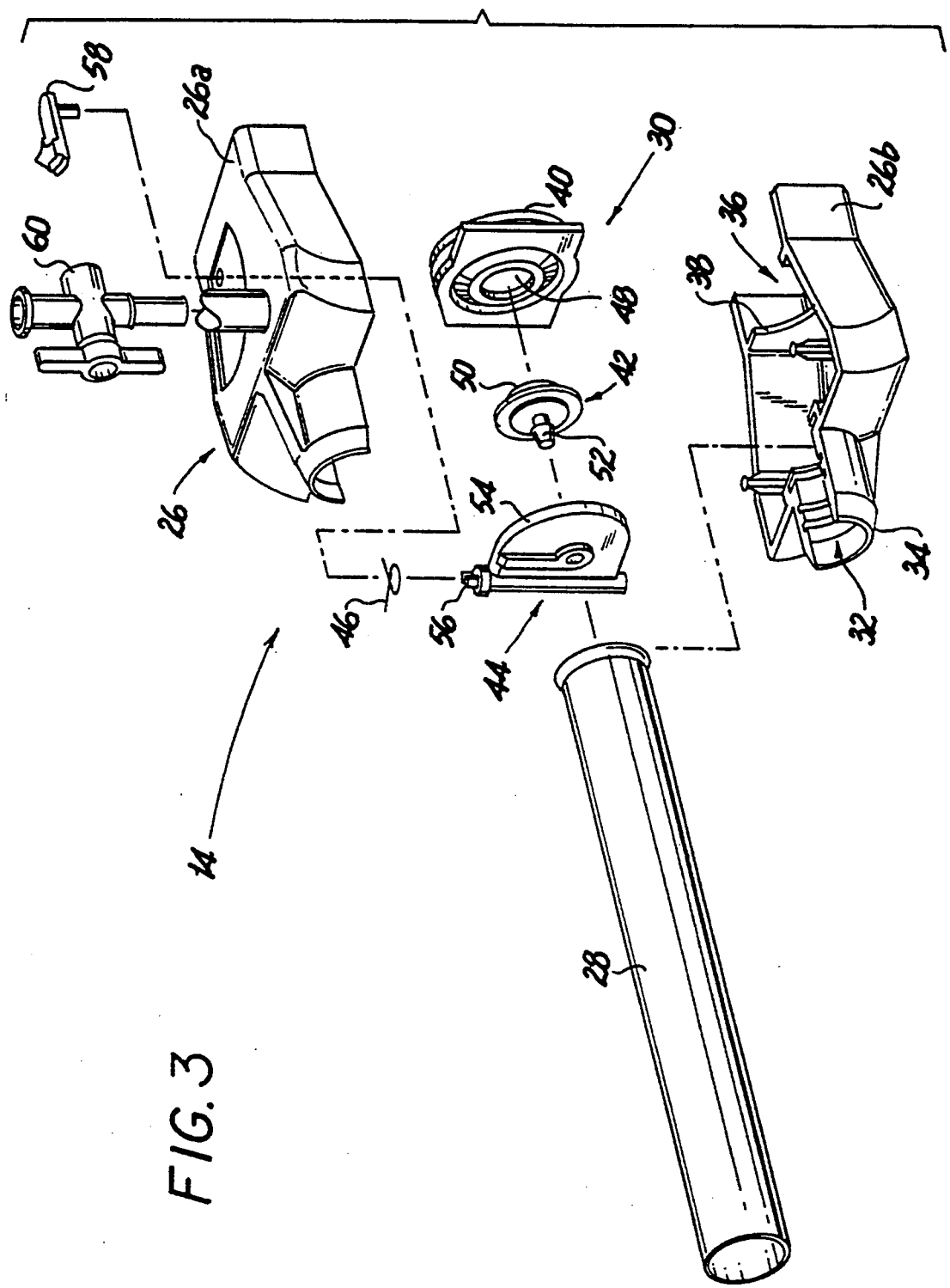
FIG. 3 is a perspective view of the cannula assembly of FIG. 1 with parts separated, illustrating the cannula housing, the cannula sleeve and a valve system.

Generally, as shown in FIG. 3, cannula housing 26 includes a top half section 26a and a bottom half section 26b suitably attached by ultrasonic welding, adhesives, or the like. However, cannula housing 26 may also be of monolithic construction. Preferably, cannula housing 26 has an open interior for mounting valve system 30. Cannula housing 26 also includes at least two openings, a first opening 32, defined by flange 34 which is formed at the distal end of housing 26, and a second opening 36, defined by flange 38 which is formed at the proximal end of housing 26. The first opening 32 permits rigid securement of the proximal end of cannula sleeve 28, and the second opening 36 is positioned in aligned communication relative with the first opening.

The valve system 30 is provided to maintain a gas tight seal within the cannula housing and will be described with reference to FIG. 3. Valve system 30 includes valve seat 40, valve plug 42, valve arm 44 and biasing spring 46. Valve seat 40 is configured and dimensioned for mounting in flange 38 of cannula housing 26. Valve seat 40 defines an aperture 48 extending therethrough which communicates with the first and second openings, 32 and 36 respectively, and is positioned in alignment therewith. Valve plug 42 includes front face portion 50 and stem portion 52 which when secured to valve arm 44 provides a sealed engagement with valve seat aperture 48 in valve seat 40. Valve arm 44 includes valve plate 54 and post 56 and is pivotally mounted within cannula housing 26 via post 56. Biasing spring 46 is positioned on post 56 and within the interior wall of cannula housing 26 to bias valve plug 42 toward a position of engagement with valve seat 40 to effect a gas tight seal. A more detailed description of the valve system described herein, and its operation, is provided in commonly assigned, U.S. Pat. No. 4,943,280 to Lander, which is incorporated herein by reference.

Cannula assembly 14 also includes desufflation lever 58 which is pivotally secured to cannula housing 26 and is provided to manually actuate valve arm 44 for gas desufflation through the cannula assembly. Stopcock type valve 60 is mounted to cannula housing 26 to permit selective insufflation or desufflation of the body cavity prior to performing the surgical procedures.

Figure 4:
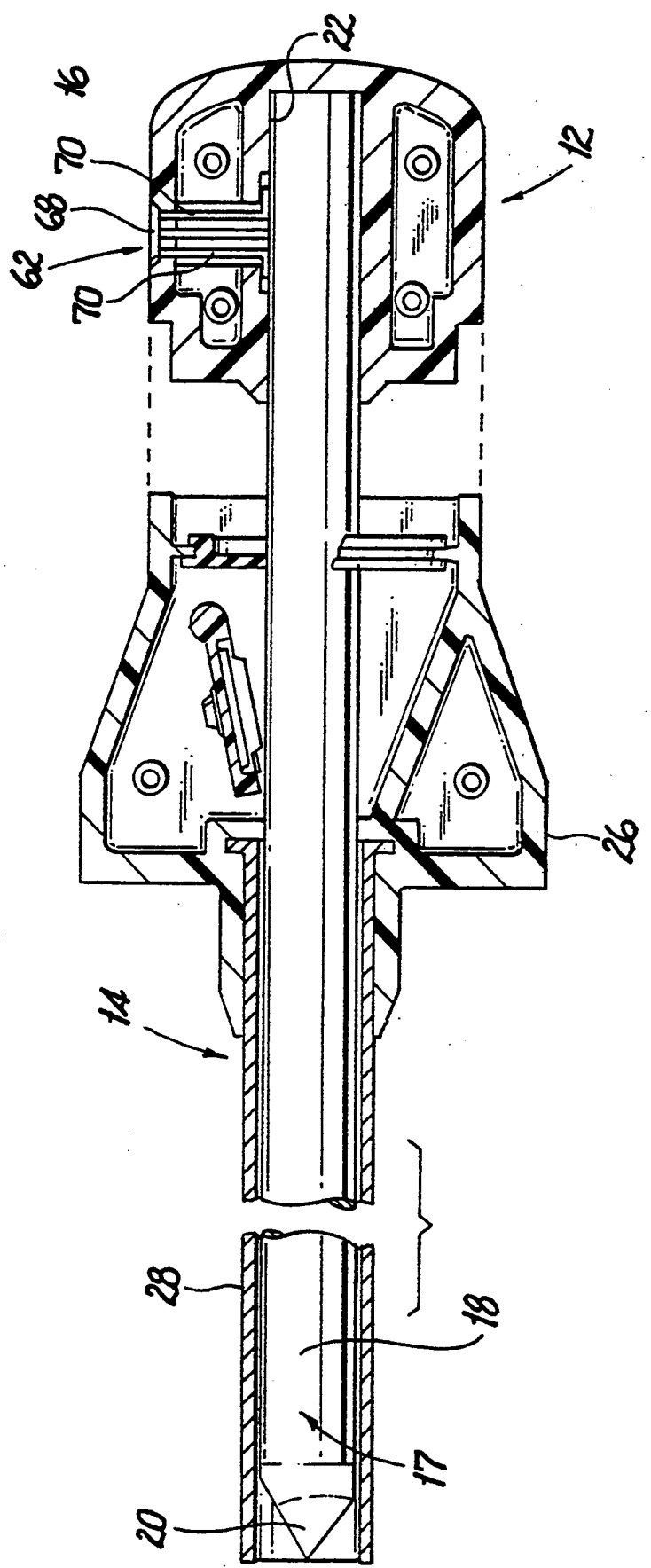
FIG. 4 is a top view in partial cross-section similar to FIG. 2, illustrating an alternative embodiment of the trocar assembly of FIG. 1 having a conductive obturator shaft and an insulating cannula sleeve.

In an alternative embodiment of the trocar assembly, obturator sleeve 24 is omitted and cannula sleeve 28 is fabricated from an insulating material, such as PTFE, as shown in FIG. 4. In this configuration, cannula sleeve 28 limits the exposure of the conductive path and acts to break the circuit between obturator tip 20 and the body tissue when the tip penetrates the body tissue, as will be described in more detail below.

The electrical connections for one embodiment of the trocar assembly of the present invention will now be described with reference to FIGS. 2 and 5. Electrical connection port 62 is positioned within obturator housing 16 and is provided to facilitate an electrical connection between obturator shaft 18 and indicator 64, such as an ohmmeter, via conductor 66. Preferably, connection port 62 includes female receptacle 68 and intermediate conductors 70 which are secured to receptacle 68 at one end and obturator shaft 18 at the other end, as shown in FIG. 2. Intermediate conductors 70 may be secured to obturator shaft 18 by solder, welds, conductive adhesives and the like.

As noted above, conductor 66 provides the electrical connection between connection port 62 and ohmmeter 64. Ohmmeter 64 is also connected to the body tissue via conductor 72. Conductor 72 is secured to conductive plate 74 which is firmly secured to the body tissue by a suitable adhesive, such as surgical tape 76, so that an electrical connection is maintained between ohmmeter 64 and the body tissue. Engagement of obturator tip 20 with the body tissue completes the circuit therebetween. In an alternative embodiment, conductive plate 74 may be an elongated plate positioned under a patient such that the weight of the patient maintains the electric connection between the plate and the body tissue.

Figure 6:
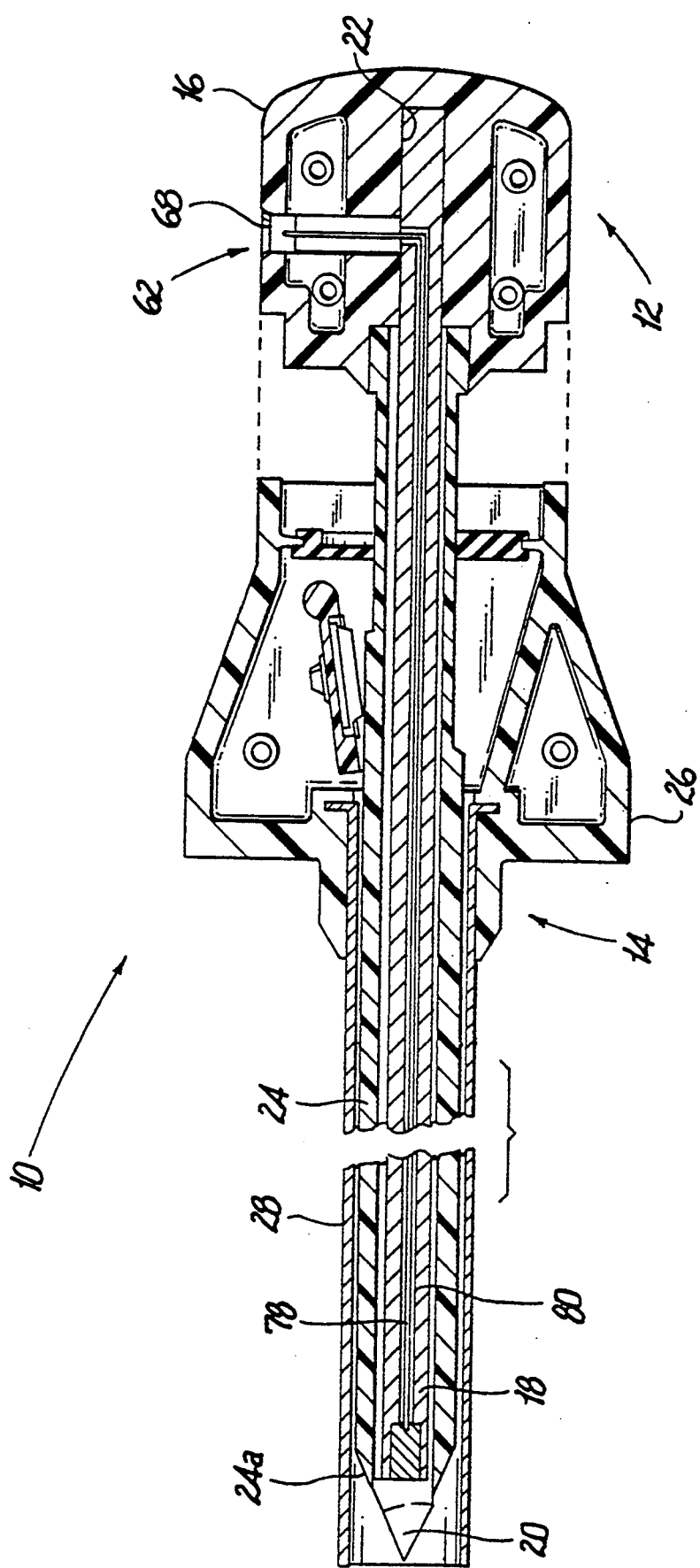
FIG. 6 is a top view in partial cross-section similar to FIG. 2, illustrating an alternative embodiment for the electrical connections for the conductive obturator tip of the present invention.

In another alternative embodiment, shown in FIG. 6, obturator tip 20 may be fabricated from an electrically conductive material and wire 78 may be inserted through channel 80 in obturator shaft 18 and connected directly to obturator tip 20. The other end of wire 78 is connected directly to receptacle 68 as shown. In this alternative embodiment, obturator shaft 18 may be fabricated from an insulating material.

Figure 7:
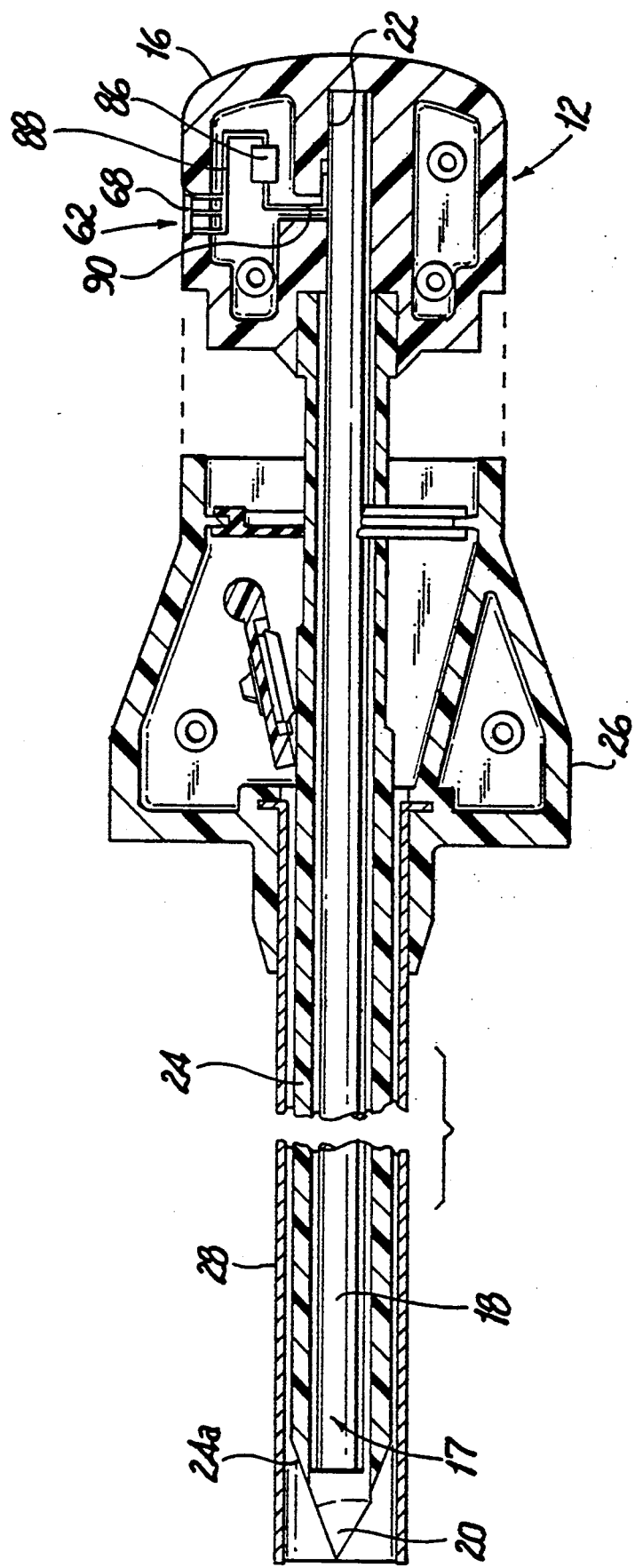
FIGS. 7 and 8 illustrate another alternative embodiment of the trocar assembly of the present invention having an internal energy source and external indicator.
Figure 8:
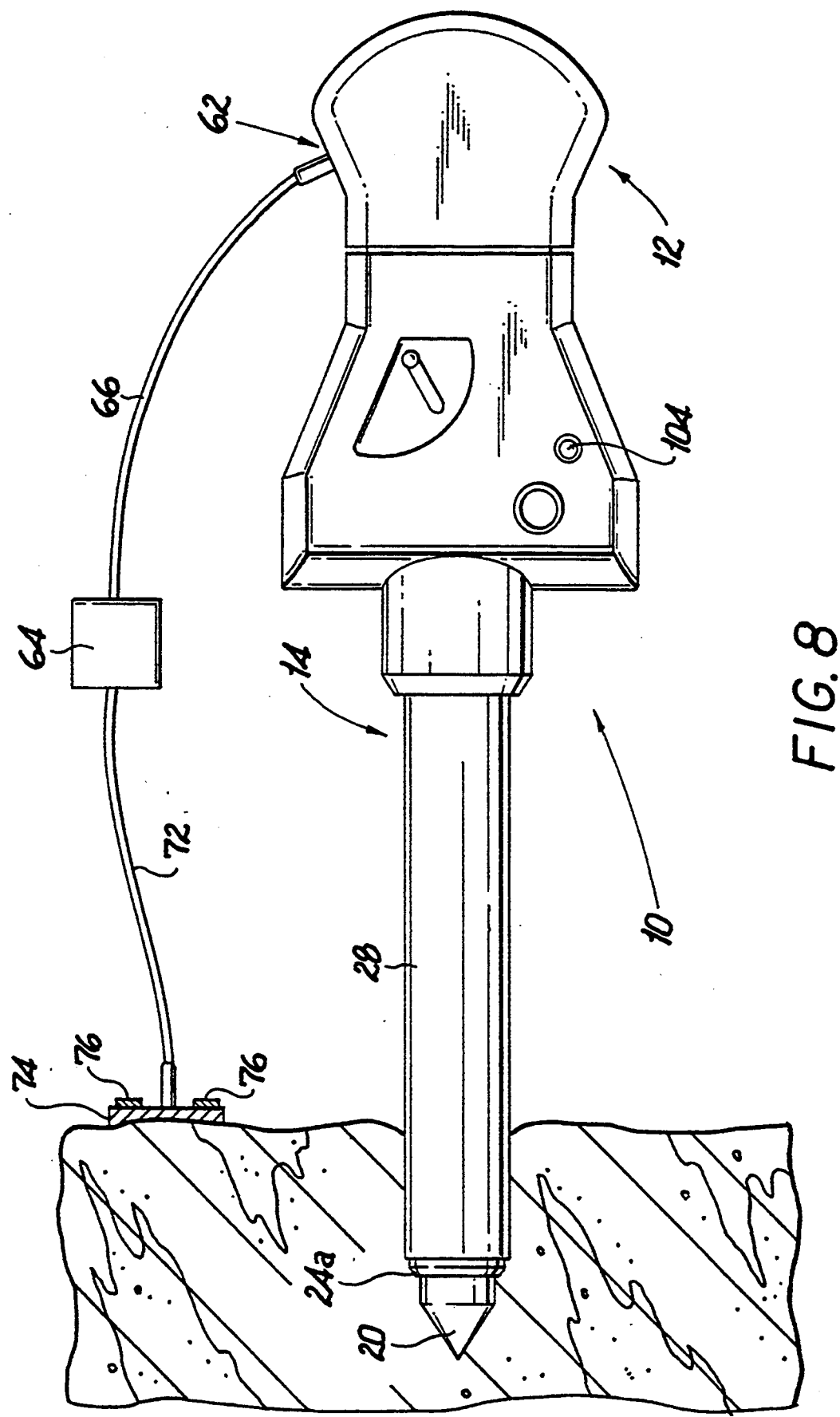

Embodiments of the trocar assembly of the present invention having internal energy sources are shown in FIGS. 7–10. In the embodiment of FIGS. 7 and 8, receptacle 68 of connection port 62 is connected to one terminal of an energy source, such as battery 86, via conductor 88 and the other terminal of battery 86 is connected to obturator shaft 18 via conductor 90. In this configuration, indicator 64 shown in FIG. 8 may be a light indicator, such as an LED, or an audible indicator such as a speaker or beeper, which is activated when obturator tip 20 engages the body tissue to complete the circuit between the energy source, the indicator and the body tissue. Upon penetration of the body tissue, the above circuit is interrupted causing indicator 64 to deactivate, e.g., the LED turns off, as will be described in more detail below.

Figure 9:
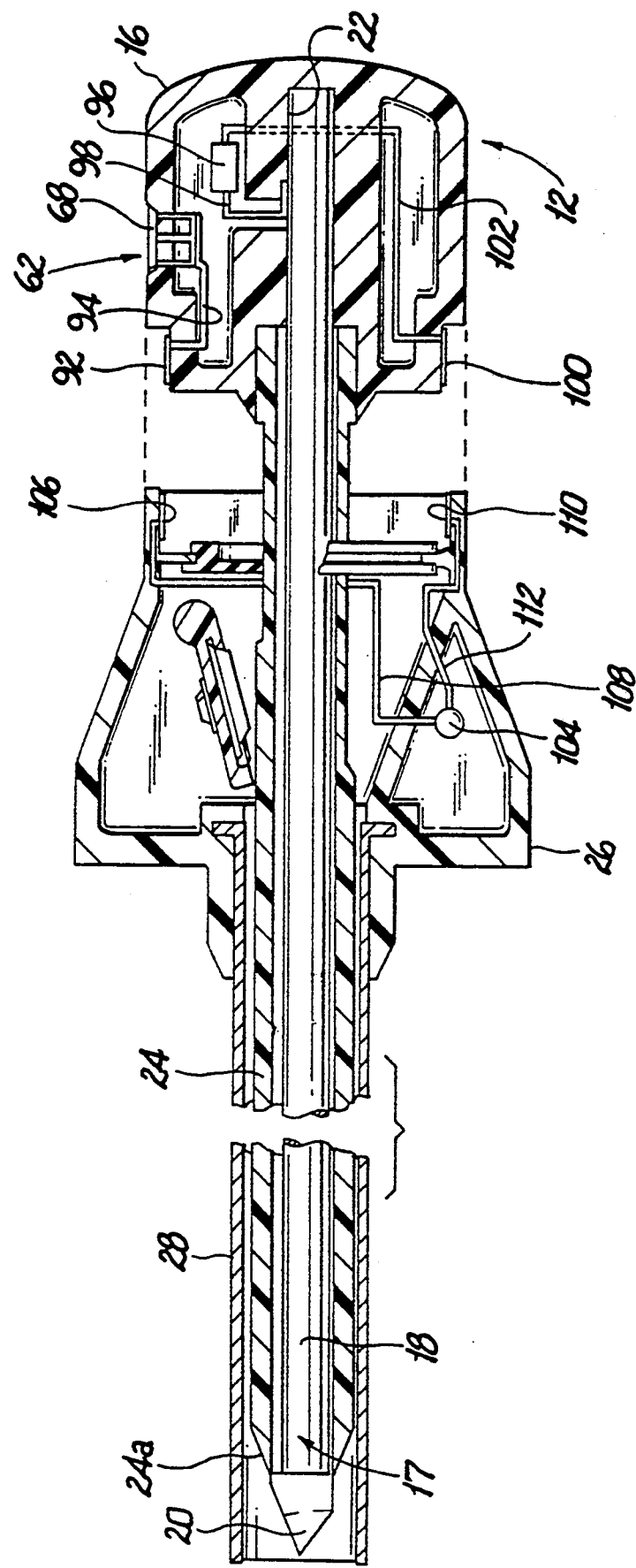
FIGS. 9 and 10 illustrate another alternative embodiment of the trocar assembly of the present invention having an internal energy source and indicator.
Figure 10:
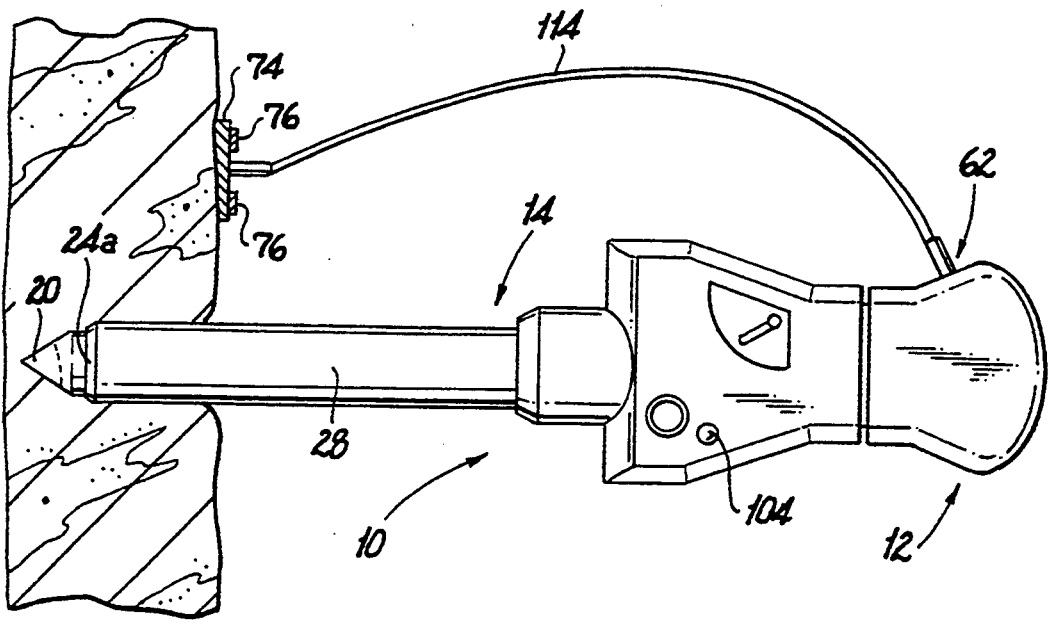

In the embodiment of FIGS. 9 and 10, the energy source and the indicator are positioned within the trocar assembly of the present invention. As shown, receptacle 68 is connected to contact plate 92 via conductor 94. An energy source, such as battery 96, has one terminal connected to obturator shaft 18 via conductor 98 and another terminal connected to contact plate 100 via conductor 102. Preferably, indicator 104, such as an LED, or a speaker or beeper, is positioned within cannula housing 26 to allow either easy viewing by the surgeon or to prevent the muffling of the speaker when penetrating the body tissue. Indicator 104 has one terminal connected to contact plate 106 via conductor 108 and another terminal connected to contact plate 110 via conductor 112. When obturator housing 16 is interfitted with cannula housing 26, contact plate 92 engages contact plate 106 and contact plate 100 engages contact plate 110 to provide the electrical connections between receptacle 68, battery 96 and indicator 104.

Referring to FIG. 10, when penetrating the body tissue, a conductor 114 is provided between the body tissue and connector port 62 so that when obturator tip 20 engages the body tissue the circuit between battery 96, indicator 104 and the body tissue is completed. Completing the circuit activates indicator 104, e.g., lighting the LED. Upon penetration of the body tissue, the above circuit is interrupted causing indicator 104 to deactivate, as will be described in more detail below.

Figure 11:
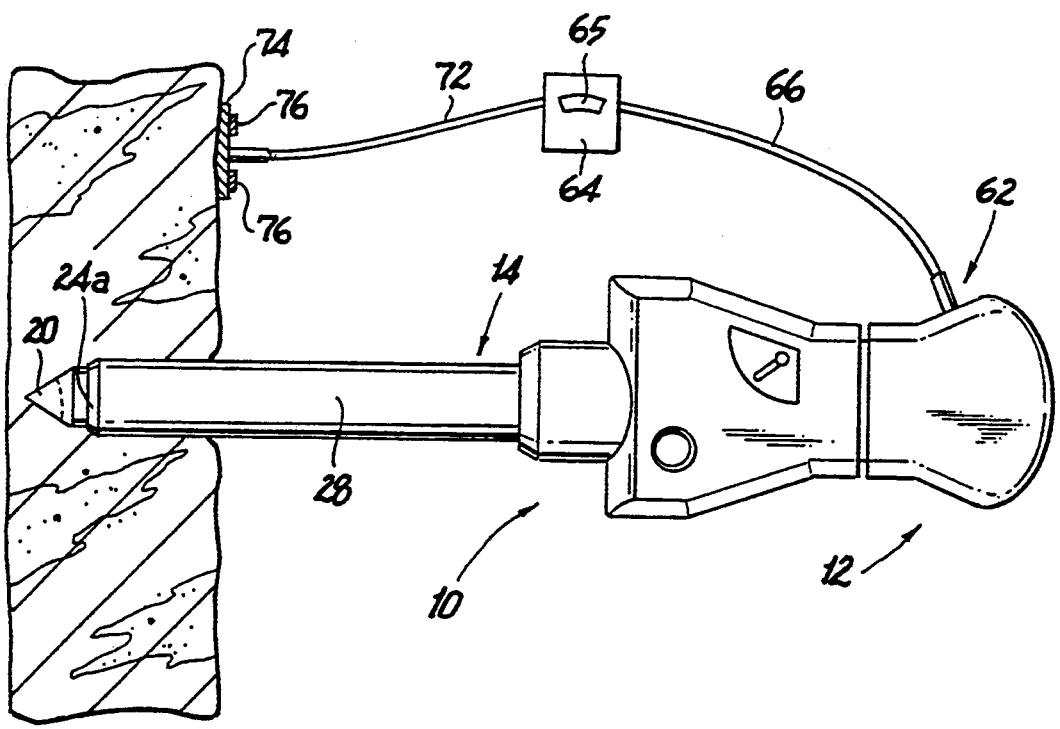
FIG. 11 is a top plan view of the trocar assembly of FIG. 1 without the stopcock, illustrating partial penetration of the trocar assembly through the body tissue and the connections between an electrical measuring instrument, the body tissue and the trocar assembly.

In operation, the indicator, e.g., ohmmeter 64 or LED 104, is connected between trocar assembly 10 and the body tissue as shown in FIGS. 11 and 12. The surgeon then applies pressure to the proximal end of trocar assembly 10, causing obturator tip 20 to penetrate the body tissue. Engagement of obturator tip 20 with the body tissue, shown in FIG. 11, completes the circuit between the needle assembly, the indicator and the body tissue so that a current flows from obturator tip 20 through the body tissue and the indicator via conductors 66 and 72. In the embodiment where the indicator is an ohmmeter, ohmmeter 64 then measures the resistance between obturator tip 20 and the body tissue, which can be visually observed from display 65 on ohmmeter 64.

Preferably, the current flowing through obturator tip 20 and/or obturator shaft 18 and the body tissue is in the microamp range so as to prevent cutting and/or cauterization of the body tissue. Typically, the current is within the range of between about 1 microampere and about 12 microamperes, preferably about 3 to about 10 microamperes. However, in instances where cutting and/or cauterization of the body tissue is desired or necessary, the current through the body tissue may be increased to accomplish the desired cutting and/or cauterization effect. It should be noted that in instances where the current level is sufficient to cut body tissue, obturator tip 20 need not be pointed or beveled to facilitate penetration of the body tissue.

Once obturator tip 20 of obturator shaft 18 completely penetrates the body tissue, shown in FIG. 12, the distal end 24a of obturator sleeve 24 prohibits the tip from further contact with the body tissue to inhibit or break the circuit. As a result, ohmmeter 64 will see infinite or very high resistance between the obturator tip and the body tissue, which can be visually observed from the ohmmeter display, thus indicating that the obturator tip has entered the body cavity. In addition, ohmmeter 64 may provide an audible indication via speaker 67 when the obturator tip penetrates the body tissue i.e., when the circuit resistance exceeds the appropriate value.

As noted above, in instances where the indicator is an LED, the LED will turn off when the circuit is inhibited, and in instances where the indicator is a speaker or beeper the sound emanating therefrom will stop when the circuit is inhibited.

Figure 5:
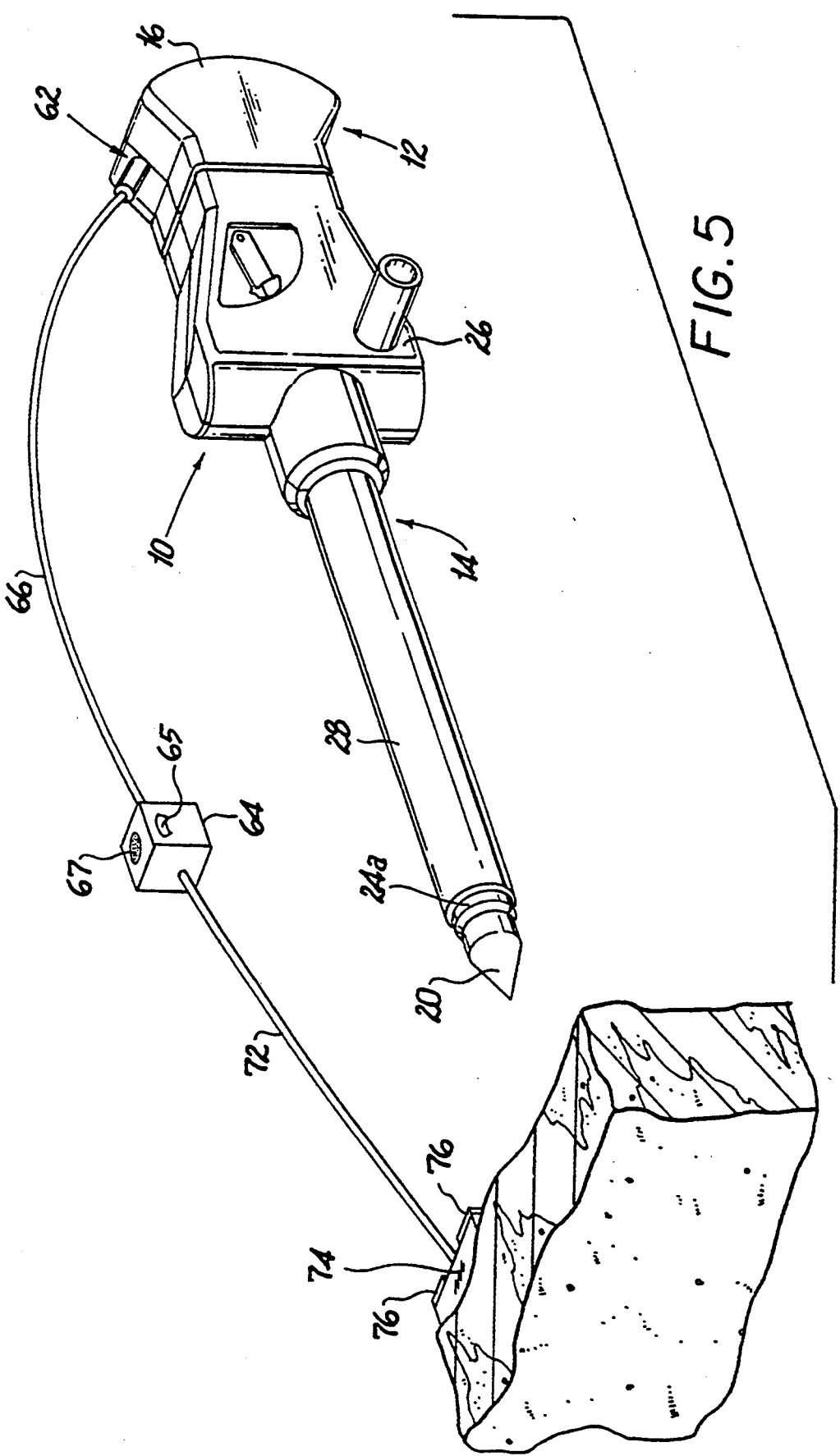
FIG. 5 is a perspective view of the trocar assembly of FIG. 1, illustrating the electrical connections between the obturator housing, an ohmmeter and the body tissue.
Figure 15:
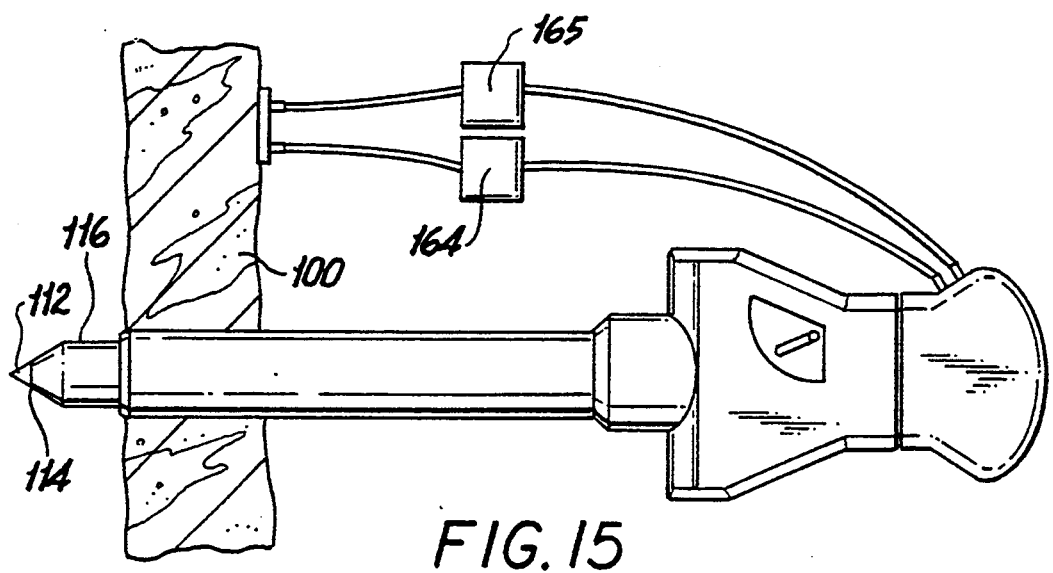
FIG. 15 is a perspective view of the trocar assembly of FIG. 13, illustrating the electrical connections between the obturator housing, two ohmmeters and the body tissue.

Another embodiment shown in FIGS. 13, 14 and 15 is a modification of the embodiment of FIG. 5 to have two indicator circuits. However, it is understood that either the embodiment of FIG. 1 or that of FIG. 5 may be modified to have two indication circuits.

The trocar tip has co-axial distal tip point 112 and tip proximal portion 116 separated by an annular region of insulation 114. First and second circuits would be each connected to a respective tip point 112 or tip proximal portion 116. Tip point 112 and the first circuit will indicate the penetration of the tip point 112 through the tissue 100. When an ohmmeter 164 associated with tip point 112 reads no current the first circuit is broken. This indicates the tip point 112 is in the cavity. When an ohmmeter 165 associated with proximal tip portion 116 reads no current, the second circuit is broken. This indicates full penetration of the obturator tip. Thus, the trocar obturator may be withdrawn with its sleeve 122 from its Cannula 120.

Figure 16:
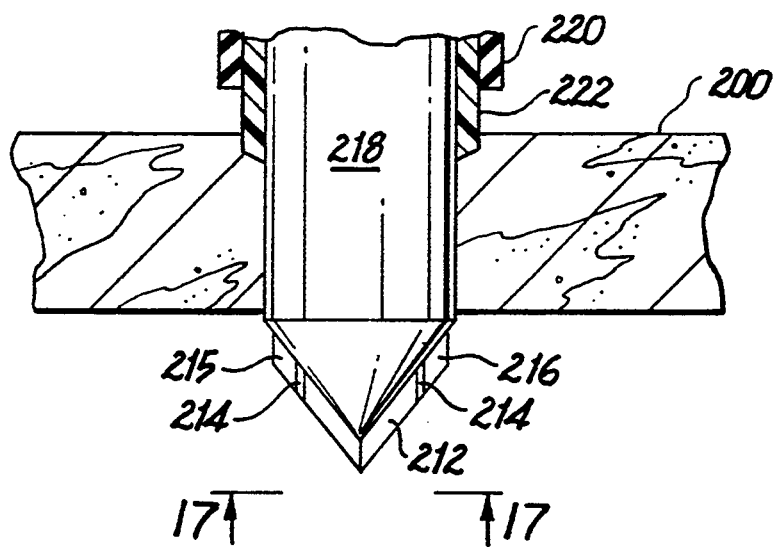
FIG. 16 is a partial cross-section of the distal end of another embodiment of the present invention.
Figure 17:
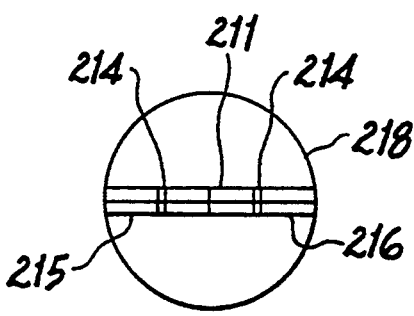
FIG. 17 is a view 17—17 of a portion of FIG. 16.
Figure 18:
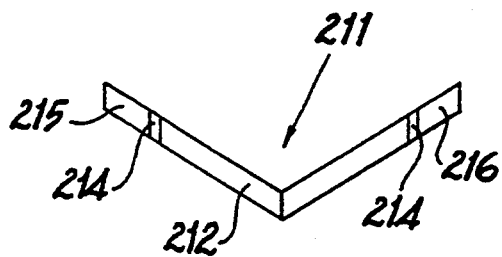
FIG. 18 is a view of a blade of FIG. 16.

A variation of this embodiment, shown by FIGS. 16, 17 and 18, employs a trocar blade 211 having three blades 212, 215, and 216 extending from a polymer base 218. The distal tip blade 212 is separated from the proximal outer blades 215, 216 by insulation 214. A first circuit would be attached to the distal tip blade 212. A second circuit would be attached to outer proximal blade 215 or outer proximal blade 216 or both. When the distal tip blade 212 passes through the tissue 200 an indicator, such as ohmmeter 164 associated with the first circuit would read no current. When the outer proximal blades 215, 216 pass through the tissue 200 an indicator, such as ohmmeter 165, associated with the second circuit would read no current. Thus, indicating full penetration of the obturator tip.

It will be understood that various modifications can be made to the embodiments of the present invention herein disclosed without departing from the spirit and, scope thereof. For example, various sizes of the instrument are contemplated, as well as various types of conductive and insulating materials. Also, various modifications may be made in the configuration of the parts. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. A method for penetrating body tissue comprising the steps of:

providing a trocar having an insulating cannula assembly and an obturator assembly, said obturator assembly having a first electrically conductive path between a proximal end portion of said obturator assembly and a conductive distal point of a distal end portion of said obturator assembly, a second electrically conductive path between said proximal end portion of said obturator assembly and a conductive proximal tip portion of said distal end portion, said distal end portion being configured to penetrate body tissue, and said obturator assembly having an insulator positioned at said distal end portion between said conductive distal tip and said conductive proximal tip portion for interrupting current through said first conductive path and an insulator positioned adjacent said distal end portion for interrupting current through said second conductive path;

providing first indicating means between said first conductive path and body tissue;

providing second indicating means between said second conductive path and body tissue;

applying current to said first and second conductive paths such that said current passes through said conductive paths and the body tissue when said distal end portion of said obturator assembly contacts the body tissue; and penetrating the body tissue with said trocar such that said first and second indicating means indicate flow of said current when penetrating the body tissue and cease to indicate said current flow when the body tissue is penetrated.

2. The method according to claim 1, wherein said current is a low-level current to prevent electrical cutting or cauterization of the body tissue.

3. The method according to claim 2 wherein said current ranges between about 1 microampere and about 12 microamperes.

4. The method according to claim 3 wherein said current ranges between 3 microamperes and about 10 microamperes.

* * * * *